United States Patent [19]

Smiley

[11] 4,331,812
[45] May 25, 1982

[54] TREATMENT OF DIBASIC ESTERS WITH ALKALI METAL METHYLATES

[75] Inventor: Robert A. Smiley, Wilmington, Del.

[73] Assignee: E. I. Du Pont de Nemours and Company, Wilmington, Del.

[21] Appl. No.: 202,250

[22] Filed: Oct. 30, 1980

[51] Int. Cl.³ .............................................. C07C 67/56
[52] U.S. Cl. ..................................... 560/191; 560/190
[58] Field of Search ................................. 560/191, 190

[56] References Cited

U.S. PATENT DOCUMENTS 3,642,871  2/1972  Tholstrup et al. ................... 560/191
4,076,948  2/1978  Mims .................................... 560/191

*Primary Examiner*—Nicky Chan
*Assistant Examiner*—Vera C. Clarke

[57] ABSTRACT

Process for reducing the color forming tendency of alkanedioic acid methyl esters by contact with an alkali metal methylate.

2 Claims, No Drawings

TREATMENT OF DIBASIC ESTERS WITH ALKALI METAL METHYLATES

BACKGROUND OF THE INVENTION

1. Field of the Invention

The present invention relates to reducing the color forming tendencies of certain esters and, more particularly, to the treatment of methyl esters with an alkali metal methylate.

2. Description of the Prior Art

U.S. Pat. No. 3,642,871 issued on Feb. 15, 1972 discloses the use of an alkali metal alkoxide, e.g., sodium methylate necessarily combined with phosphorus atoms, e.g., phosphoric acid to improve the color stability of a wide variety of organic esters including diesters of aliphatic carboxylic acids, e.g., dimethyl adipate, dibutyl sebacate and diisopropyl succinate.

SUMMARY OF THE INVENTION

A process for reducing the color forming tendency of alkanedioic acid methyl esters, e.g., those esters derived from dicarboxylic acids having 4–12 carbon atoms which comprises, consists or consists essentially of contacting the esters with alkali metal methylate, preferably sodium methylate.

DETAILED DESCRIPTION OF THE INVENTION

The methyl esters to which the present invention is particularly applicable are those prepared from the acids isolated as co-products from the air oxidation of cyclic hydrocarbons to cyclic ketones and alcohols followed by the oxidation of the ketones and alcohols with nitric acid. The oxidation of cyclohexane to cyclohexanol and cyclohexanone can be conducted according to the teachings, for example, of U.S. Pat. No. 3,530,185 issued on Sept. 22, 1970. Cyclohexanol and cyclohexanone produced according to the aforementioned Patent are then oxidized with nitric acid according to the teachings of U.S. Pat. No. 3,359,308 issued on Dec. 19, 1967 and U.S. Pat. No. 3,365,490 issued on Jan. 23, 1968. Illustrative of the co-product acids that are produced along with adipic acid in the aforementioned processes are succinic acid and glutaric acid.

The preparation of alkane dicarboxylic acids having from 8 to 12 carbon atoms by the nitric acid oxidation of the corresponding alcohols and ketones is disclosed in U.S. Pat. No. 3,758,564 issued on Sept. 11, 1973. Illustrative of the co-product acids produced in this process are pimelic acid, suberic acid, azelaic acid, sebacic acid and undecanedioic acid.

The principal acids produced in the above described processes, i.e., adipic acid and dodecanedioic acid are commonly separated from the co-product acids by crystallization and the co-product acids then recovered from the mother liquor by known methods. These co-product acids can be converted to esters by known esterification processes. Even after rigorous distillation, these esters still exhibit a marked tendency to turn yellow when subjected to alkaline conditions or when heated to temperatures for which the esters are eventually employed, e.g., for the preparation of other esters and polyesters by transesterification.

The color-forming tendency of esters which are treated according to the process of the present invention is believed due to the presence of small amounts of aliphatic nitro compounds which form during the nitric acid oxidation of the ketones or alcohols and/or during acid catalyzed esterification in the presence of residual nitrate ion. These impurities co-distill with the esters; are not adsorbed to any significant extent on activated carbon and are not amenable to bleaching, e.g., with peroxides or aqueous hypochlorites.

The methylates which are operable in the present invention include sodium, potassium and lithium methylate and mixtures of the foregoing. Sodium methylate is preferred.

The method for contacting the methylate with the esters is not critical to the present invention. Adding the solid methylate to the esters with low shear stirring at ambient temperature has been found completely satisfactory. As one skilled in the art can appreciate, elevated temperatures will accelerate the reaction. The contacting may be conducted at temperatures up to 225° C. and preferably 75°–100° C. for times varying from about 0.5–2 hours. Time can be decreased as the temperature is increased. The presence of water markedly reduces the effectiveness of the methylate and it is preferred to maintain water at the lowest practical level, e.g., less than 0.1% by weight based upon the weight of the esters.

The esters should be neutral or slightly basic for optimum utilization of the methylate and for color reduction. Usually a precipitate is formed during the contact of the ester and the methylate which can if desired be removed by known methods, e.g., filtration before further processing of the treated esters.

The amount of methylate required will, of course, depend upon the amount of color-formers present which is dictated by the conditions used in preparing the acids and/or the esters. It has been determined that 2–25 and usually about 5 parts by weight of methylate per 1000 parts by weight of ester is usually sufficient for complete reduction in color. In many instances less than one part of methylate per 1000 parts of ester can accomplish complete color reduction. In any event, the amount of methylate required is readily determined by increasing or decreasing the amount of methylate until the desired level of color is obtained. Excess methylate can be employed to assure an essentially complete reduction in color forming tendency.

The following examples are presented to illustrate but not to restrict the present invention. Parts and percentages are by weight unless otherwise specified. The color forming tendencies of the esters treated according to the process of the present invention were determined by adding two drops of a 40% by weight solution of benzyltrimethyl ammonium-hydroxide in methanol to 5 ml of esters, followed by shaking the solution. The esters reported in the Examples were treated in this manner before determining the color. Color was judged using a Hellige Color Comparator equipped with a Gardner color disc (color system of the Institute of Paint and Varnish Research). This technique measures the yellowness of samples on a scale from 1 (very light yellow) to 10 (dark yellow). A colorless sample exhibits a Gardner color of less than 1.

EXAMPLE 1

To a 500 ml flask fitted with a simple distillation head and suitable heating equipment was added 227 grams of the mixed methyl esters of succinic, glutaric and adipic acid, having the analysis set forth in Table I and a Gardner color of 4.

TABLE I

| | |
|---|---|
| Dimethyl succinate | 2% |
| Dimethyl glutarate | 71% |
| Dimethyl adipate | 27% |

This ester mixture was prepared as described hereinabove by esterification of the acids obtained by the nitric acid oxidation of a mixture of cyclohexanol and cyclohexanone followed by removal of the majority of adipic acid by crystallization.

Approximately 3.5 grams of sodium methylate was introduced into the flask. The resultant slurry was heated with stirring at 75° C. for one hour whereupon the contents of the flask turned yellow. This ester was then distilled with essentially no fractionation under 25 mm Hg vacuum. Approximately 215 grams of distillate having a Gardner color of <1 was collected.

EXAMPLE II

A mixture of $C_{7-12}$ straight chain dibasic acids recovered from the nitric acid oxidation of cyclododecanone and cyclododecanol as described hereinabove were esterified with methanol using a dodecylbenzene sulfonic acid catalyst. The resultant esters were then distilled under 1 mm Hg pressure and a distillate boiling in the range of 95°–140° C. and having a Gardner color of 9 was recovered. This ester distillate had the composition given in Table II.

TABLE II

| | | | |
|---|---|---|---|
| Dimethyl pimelate | 0.5% | Dimethyl sebacate | 7.5% |
| Dimethyl suberate | 1.5% | Dimethyl undecandioate | 48.4% |
| Dimethyl azelate | 4.2% | Dimethyl dodecandioate | 37.9% |

To 124 parts of the ester distillate was added 2 parts of sodium methylate with mild agitation at room temperature. The mixture was then distilled at <1 mm Hg pressure. After a small foreshot which was discarded, 104 parts of treated esters were collected which had a Gardner color of less than 1.

I claim:

1. A method of reducing the color-forming tendency of methyl esters obtained from alkanedioic acids having 4–12 carbon atoms produced by the nitric acid oxidation of cycloaliphatic hydrocarbons selected from the class consisting of ketones, alcohols and mixtures of the foregoing which method consists of contacting said esters with an alkali metal methylate and thereafter recovering the thus treated esters.

2. The process of claim 1 wherein the methylate is sodium methylate.

* * * * *